United States Patent [19]

Janssen et al.

[11] 4,024,588

[45] May 24, 1977

[54] ARTIFICIAL JOINTS WITH MAGNETIC ATTRACTION OR REPULSION

[75] Inventors: Rainer Janssen, Munich, Germany; Bernhard G. Weber, Saint Gall, Switzerland

[73] Assignee: Allo Pro A.G., Switzerland

[22] Filed: Oct. 3, 1975

[21] Appl. No.: 619,525

[30] Foreign Application Priority Data

Oct. 4, 1974 Germany .......................... 2447383

[52] U.S. Cl. .................................. 3/1.91; 3/1.911; 3/1.912; 128/92 C
[51] Int. Cl.$^2$ .......................................... A61F 1/24
[58] Field of Search ........................... 3/1.9–1.913, 3/1; 128/92 C, 92 CA

[56] References Cited
UNITED STATES PATENTS

| 3,140,712 | 7/1964 | Hunter | 3/1.91 X |
| 3,370,305 | 2/1968 | Goott et al. | 3/1.5 |
| 3,521,302 | 7/1970 | Muller | 3/1.91 |
| 3,694,820 | 10/1972 | Scales et al. | 3/1.91 |
| 3,889,300 | 6/1975 | Smith | 3/1.91 |

*Primary Examiner*—Ronald L. Frinks
*Attorney, Agent, or Firm*—Craig & Antonelli

[57] ABSTRACT

An artificial joint for implantation into the living body comprises a head portion adapted to be anchored in one bone of the body and a socket portion adapted to be anchored in another bone. One of the head and socket portions includes a permanent magnet and the other portion either a magnetizable element or another permanent magnet. The two interacting magnetic elements may be polarized for either attraction or repulsion. The head and socket portions are shaped to permit translatory movements relative to each other in addition to rotary movements of the head portion about at least one axis of rotation.

22 Claims, 9 Drawing Figures

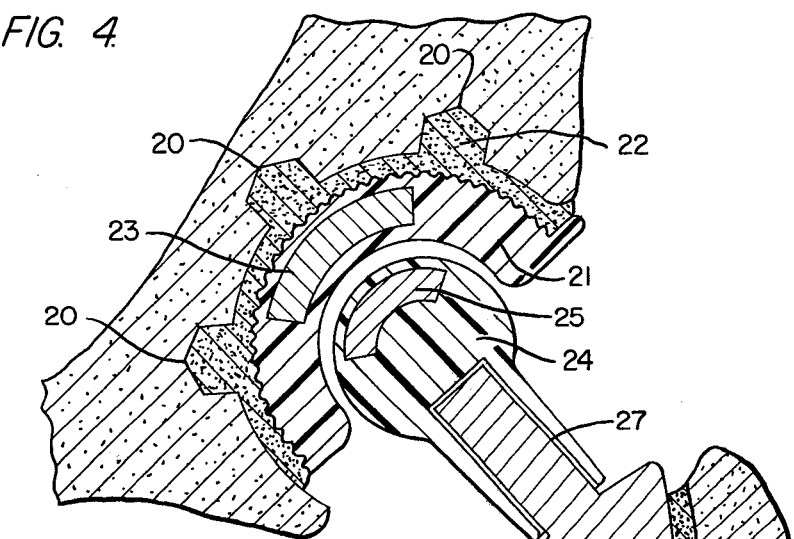
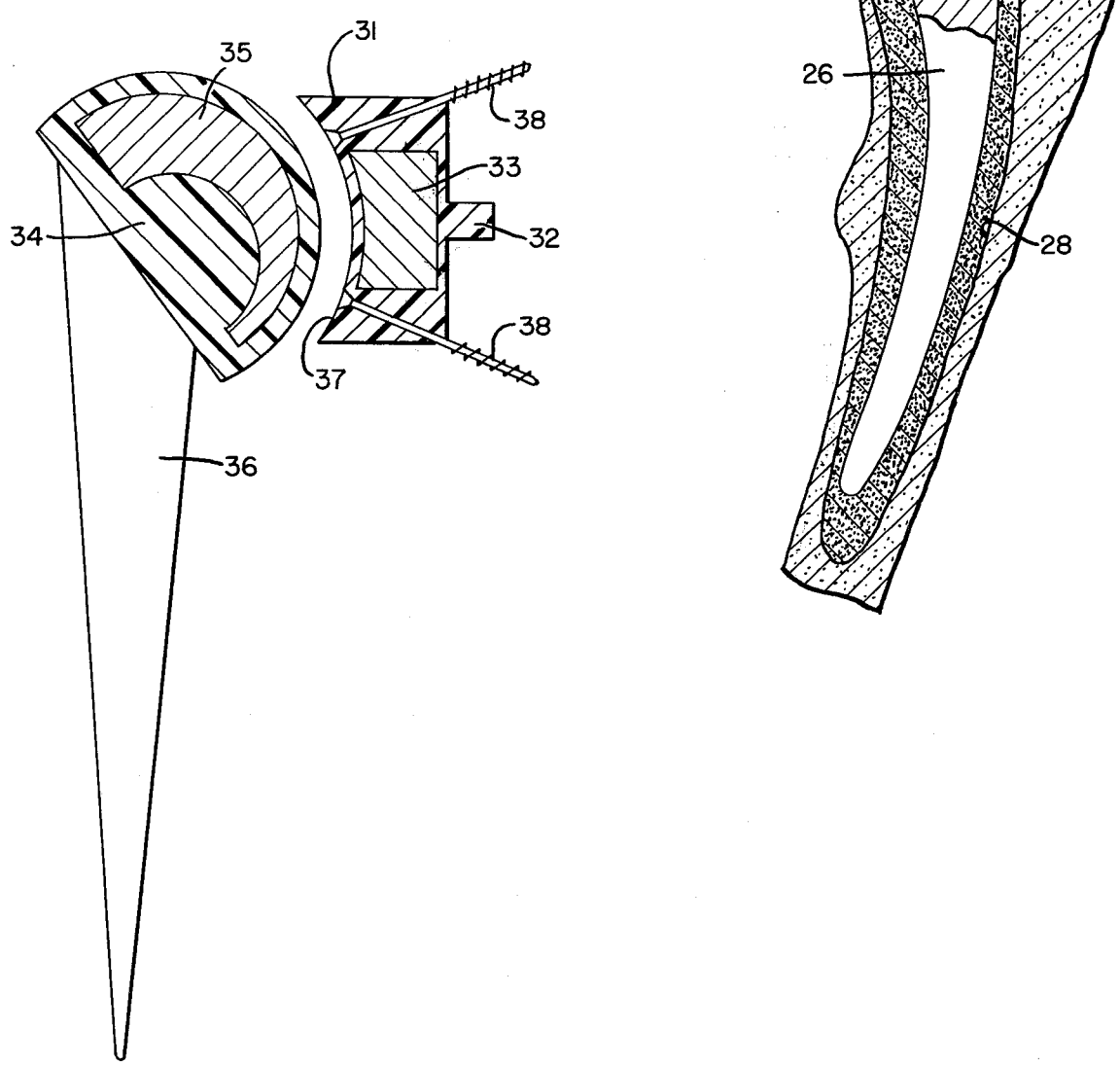

ARTIFICIAL JOINTS WITH MAGNETIC ATTRACTION OR REPULSION

The present invention relates to an artificial joint adapted for implantation into the living body.

A number of artifical joints are known. For instance, an artificial knee joint has been devised which includes a femoral ball portion and a tibial socket portion, the ball portion comprising a pair of spaced spherical segments and the socket portion comprising a pair of spaced socket segments. The concave partial spherical surfaces of the socket segments and the convex surfaces of the ball segments have the same center of curvature. A space is retained between the segments of the joint portions for receiving the front and rear cruciates which keep the joint portions connected with the respective bones in mutual engagement.

This known knee joint permits only a hinge movement of the joint portions relatively to each other, which is not in accordance with the conditions in the natural knee joint where a translatory movement takes place in addition to a hinge movement of the joint portions.

The above-mentioned known artificial joint has the further disadvantage that cannot be used in case the ligaments are destroyed, as there is then no means to hold the joint portions together.

Another artificial joint is known, the parts of which are connected by means of a rigid pin. This joint has the disadvantage that it allows a relative rotation of the joint portions about only one axis so that this joint cannot be used to replace a natural knee or shoulder joint where a more universal movement of the two joint portions relatively to each other is required. It is a further problem encountered with an artificial joint of this type that any shocks imparted to it are transmitted without attenuation.

German Pat. No. 320,756 issued Apr. 28, 1920, describes a joint for artificial limbs wherein the two interacting surfaces of the joint portions are magnetized so as to attract each other.

On the one hand, this joint is described only for use with artificial limbs rather than for being implanted into the living body. On the other hand, while no details are disclosed in that specification, it is understood that the socket and ball portions of the joint are only rotatable with respect to each other but do not permit any other movements occurring with the various natural joints. A problem which this joint has in common with all other known artifical joints resides in the wear caused by the relatively considerable weight of the body.

Another problem common to all artificial joints previously suggested is the fact that they have been made from metal, synthetic resin or other relatively hard and inelastic materials so that any shocks imparted to a portion of the body are transmitted through the link to the rest of the body. Such inelastically transmitted shocks are particularly harmful as they affect the delicate connections between the joint portions and the respective bones.

It is thus an object of the invention to provide an artificial joint adapted for implantation into the living body in which the above-mentioned difficulties are largely obviated.

More specifically, it is an object of the invention to provide an artificial joint which permits a greater freedom of movement, resulting in an improved simulation of the respective natural joint than the previous artificial joints.

It is a further object of the invention, to reduce the wear of the two joint portions movable relative to each other.

Another object of the invention is the provision of an artificial joint adapted for implantation into the living body which has a certain resiliency so as to protect the connections between the joint portions and the respective bones and to prevent those connections as well as the bones themselves from becoming damaged by excessive shocks.

Briefly, an artificial joint for implantation into the living body in accordance with the present invention comprises a head portion and a socket portion each adapted for being fixedly connected to a respective bone. At least one of the head and socket portions includes at least one permanent magnet, while the respective other portion consists at least partly of a ferromagnetic material. The head and socket portions are shaped such that they allow their mutual pivotal movement about at least one axis as well as their mutual translatory movement in at least one direction transverse of the said axis. It is preferred to employ permanent magnets in both the head portion and the socket portion in order to achieve the relatively high magnetic force required. For the majority of joints, namely the knee joint, shoulder joint, interphalangeal joint, wrist joint and elbow joint, the attractive force of the permanent magnet or permanent magnets will be used. In these cases, it is advantageous that the surfaces of the two joint portions co-operating with each other have different shapes and/or areas to allow excessive shocks to create a subluxation with subsequent relocation, thus preventing such excessive shocks from being transmitted to the anchorages of the joint portions in the respective bones. On the other hand, it is advantageous for an artificial hip joint or ankle joint to include at least one permanent magnet in each joint portion and to polarize the permanent magnets such that the two joint portions repel each other. In such case, an excellent resiliency and damping between the two joint portions is achieved, and wear is kept at a minimum. Similar joint-like assemblies including permanent magnets polarized for repulsion may be employed to replace intervertebral disks.

The invention will now be described in more detail with reference to the drawings in which preferred embodiments of the invention are shown. In the drawings:

FIG. 4 is a section through a hip joint, in which portions of the pelvis and femur are shown;

FIG. 5 shows a diagrammatic section of a shoulder joint; and

FIGS. 6 to 9, respectively illustrate sections of an interphalangeal joint, a wrist joint, an elbow joint and an ankle joint.

DETAILED DESCRIPTION OF PREFERRED EMBODIMENTS

Figure 1:
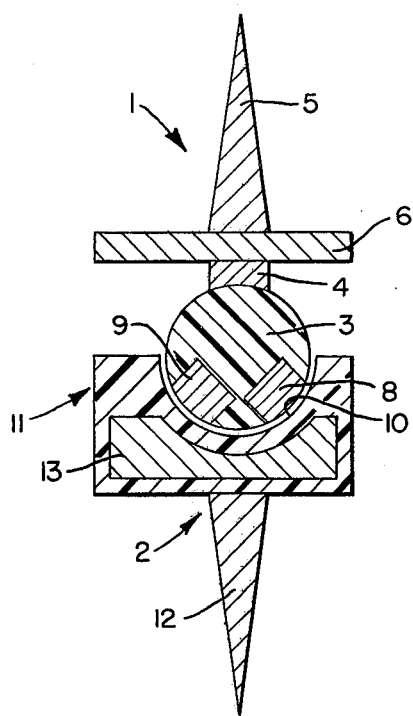
FIG. 1 is a diagrammatic cross-sectional view of a basic joint structure in accordance with the present invention, including a spherical head and a hollow-spherical socket.

In accordance with the basic structure shown in FIG. 1, an artificial joint according to the invention includes a head portion 1 and a socket portion 2. The portions 1 and 2 are implanted into the living body by surgical methods to replace a diseased or disabled joint.

The head portion 1 of the artificial joint has a head 3, a neck 4 and a shaft 5 connected to the neck 4 with a supporting flange 6 disposed between the neck 4 and the shaft 5. The surgeon mounts the shaft 5 in the respective portion of a bone (not shown).

The head 3 is made of a material tolerated by the body, such as a suitable organic high-resistance polymer, a suitable metal alloy or ceramic. Permanent magnets 8 and 9 are embedded into that material. The permanent magnets 8 and 9 are disposed as closely as possible to the portion of the convex surface of the head 3 received by a concave portion 10 of the socket portion 2. The permanent magnets 8 and 9 may consist of iron, nickel, cobalt and/or samarium or of any alloy usually employed for such purpose; alternatively, they may be made of ferrite. An alloy of cobalt and a rare earth, especially samarium, has been found to be a particularly suitable material for the permanent magnets. The neck 4, the shaft 5 and the supporting flange 6 may be made of stainless steel or another alloy suitable for such purpose, such as a cobalt-cromium alloy or the like. One end of the neck 4 is casted into the material of the head 3.

As shown in FIG. 1, the socket portion 2 includes a socket 11 and a shaft 12. Again, the shaft 12 is mounted in the respective bone by the surgeon. The socket 10 is provided with the above-mentioned concave portion 10 for receiving the head 3 of the artificial joint. The depth, angular extension and curvature of the concave portion 10 of the socket 11 is selected subject to the respective joint of the body which is to be replaced by the present artificial joint.

The socket 11 is also made from one of the above-mentioned materials tolerated by the body. At least one element 13 of ferromagnetic material is embedded in the material of the socket 11. One end of the shaft 12 may be cast into the material of the socket 11. The element 13 co-operates with the permanent magnets 8 and 9 included in the head 3 so that the portions 1 and 2 of the artificial joint are held together by the attractive force created by the permanent magnets 8 and 9.

Instead of the element 13 of ferromagnetic material, one or a number of permanent magnets may be embedded in the socket 11. In this case, the two portions 1 and 2 of the artificial joint are either attracted or repelled, dependant on the mutual polarization of the magnets 8 and 9 disposed in the head 3 and the permanent magnet or magnets disposed in the socket 11.

The embodiment of FIG. 1 has been described to illustrate certain general aspects of the invention. In the following description, a number of artificial joints will be described which are adapted to replace specific joints of the human body.

Figure 2:
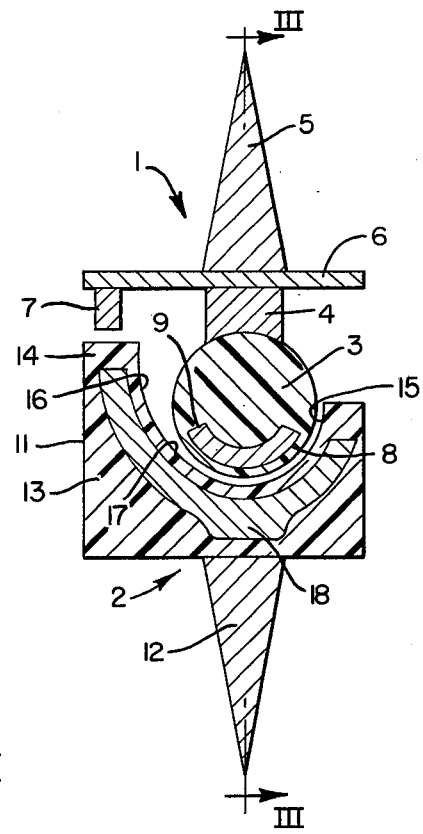
FIG. 2 is a diagrammatic sectional view similar to that of FIG. 1, illustrating an artificial knee joint.
Figure 3:
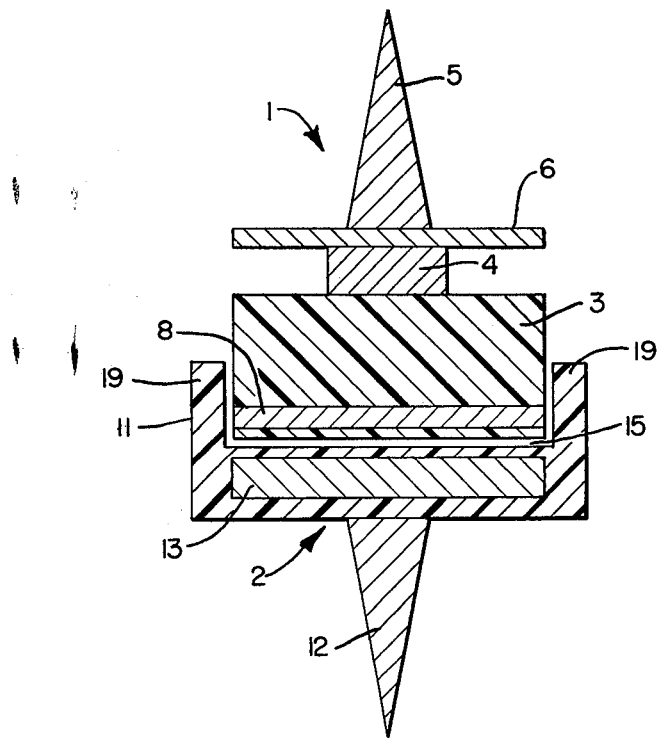
FIG. 3 is a section taken along the line III—III of FIG. 2.

In FIG. 2 and FIG. 3, an artifical knee joint is shown in a somewhat diagrammatic manner. In this case, the head 3 has a substantially cylindrical form while the socket 11 is substantially trough-shaped. The trough shape of the socket 11 is composed of three sections 15, 16 and 17 joining each other. The section 15 which receives the cylindrical head 3 in the position shown in FIG. 2, i.e. in the straight position of the knee, has a radius of curvature which is only slightly greater than that of the cylindrical portion 3. Similarly, the section 16 which receives the cylindrical head 3 when the knee is bent at approximately 90°, has a radius of curvature slightly greater than that of the head 3. The section 17 connecting the sections 15 and 16 has a radius of curvature which is essentially greater than the radius of the sections 15 and 16. Du to this shape, when bending the knee, the cylindrical head portion 3 will travel along the concave trough-shaped socket 14, rising from the section 15 towards the section 16. Simultaneously during such bending movement of the knee, the cylindrical head 3 will rotate about its longitudinal axis. This complex rotary and translatory movement of the joint much more closely simulates the movement of a natural knee joint than a simple hinge joint as provided by the prior art devices.

As indicated in FIG. 2, the head portion 3 includes a permanent magnet 8 which is shaped as part of a cylindrical shell. A generally similarly shaped element 13 is embedded in the socket 11. Regularly, when the natural knee joint is disabled in such a manner that it must be replaced by an artificial joint, the cruciates will be destroyed so that an external force is necessary to hold the two portions of the leg together. Therefore, the segment 13 may be of a magnetizable material co-operating with the permanent magnet 8 so as to produce an attractive force. To increase the magnetic force, however, the element 13 may be constituted by a second magnet polarized such that the two magnets attract each other.

As also shown in FIG. 2, the element 13 has at its lowermost location an enlarged portion 18. This enlarged portion 18 will tend to pull the magnet 8 in its lowermost position causing the joint to assume the position shown in FIG. 2, i.e. the position of the straight knee. This feature increases the stability of the leg in the standing position.

A projection 7 is provided on the flange 6 disposed between the neck 4 and the shaft 5 of the head portion 1 at the front of the knee joint. The projection 7 abuts an upper portion 14 of the socket 11 when it is attempted substantially to bend the knee joint beyond its straight position. A similar locking may be achieved by correspondingly disposing and sizing the magnets.

The magnet 8 and the element 13 should be embedded in their respective parts 3 and 11 as closely as possible to the respective spherical and trough-shaped surface to achieve strong magnetic forces. However, the spacing of the magnet 8 from its spherical surface and of the element 13 from its trough-shaped surface should be sufficient to prevent the magnet 8 and the element 13 from becoming exposed due to wear-off of the embedding material of the head 3 and the socket 11, respectively.

According to FIG. 3, the socket 11 includes lateral guide portions 19 which prevent the head 3 from becoming dislocated in its axial direction. These guide portions 19 may not be necessary, though, since the magnet 8 and the element 13 have a self-centering effect in the lateral direction.

In FIG. 4, a hip joint is shown in which the socket 21 generally has the form of a spherical shell and includes a similarly shaped permanent magnet 23. The socket 11 is fixed to the pelvis by means of a suitable cement 22 anchored by means of three bores 20 provided in the pelvis. The head 24 is substantially ball-shaped and includes a permanent magnet 25 of a similar shape as the permanent magnet 23. The head 24 is pivoted to a shaft 26 by means of a mechanical joint 27. The shaft 26 is cemented into a recess 28 previously provided in the femur. The magnets 23 and 25 are polarized such that they repel each other. A damping effect is thus achieved which prevents the shocks exerted on the leg to be transmitted to the trunk. In order to allow such damping effect, the socket 21 and the head 24 are shaped so as to permit a relative movement of the head 24 in a direction out of the socket 21. The thus provided gap between the socket 21 and the head 24 is of great practical significance in as far as the antifriction films provided on the opposite surfaces of the head 24 and the socket 21 can only be renewed by surgery.

The shoulder joint diagrammatically shown in FIG. 5 includes a generally spherical head 34 and a block-shaped socekt 31 having a concave spherical end surface 37. A permanent magnet 35 having a generally crescent-shaped cross section is embedded into the material of the head 34, the outer spherical surface of the magnet 35 conforming the surface of the head 34. The head 34 is anchored in the humerus by means of a shaft 36. The socket 31 includes a block-shaped permanent magnet 33 also having a concave end surface conforming the surface 37 of the socket 31. The socket 31 is anchored in the scapula by means of a central pin 32 and two lateral screws 38 which engage the thickened rims of the scapula. The two permanent magnets 33 and 35 are polarized so as to attract each other. The crescent shape of the magnet 35 serves to aid the lifting movement of the arm in that the cross section of the magnet 35 opposing the magnet 33 becomes larger the more the arm is lifted (which corresponds to a rotation of the head 34 in the clockwise direction in FIG. 5). Such increase in the cross section of the magnet 35 causes a corresponding increase of the magnetic attraction force, tending to counteract the increasing gravitational force.

Figure 6:
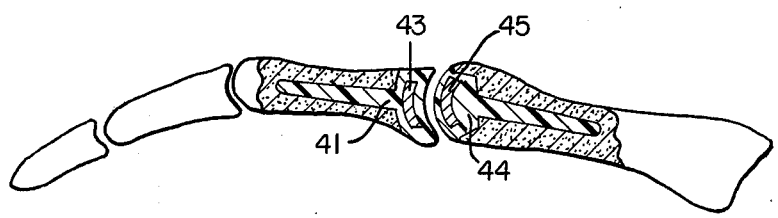
Figure 7:
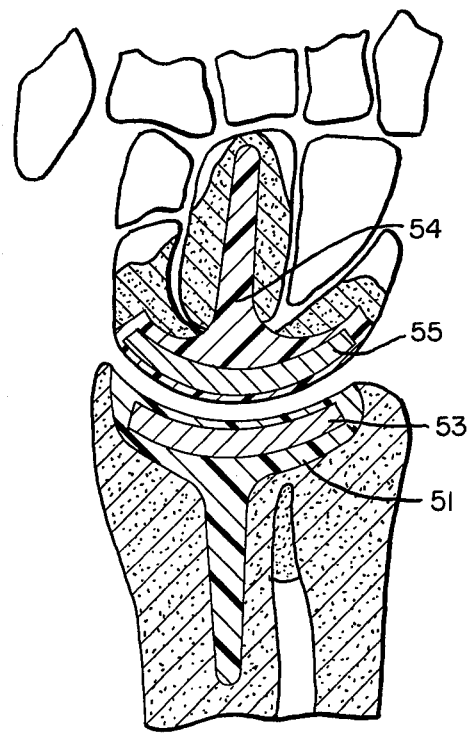
Figure 8:
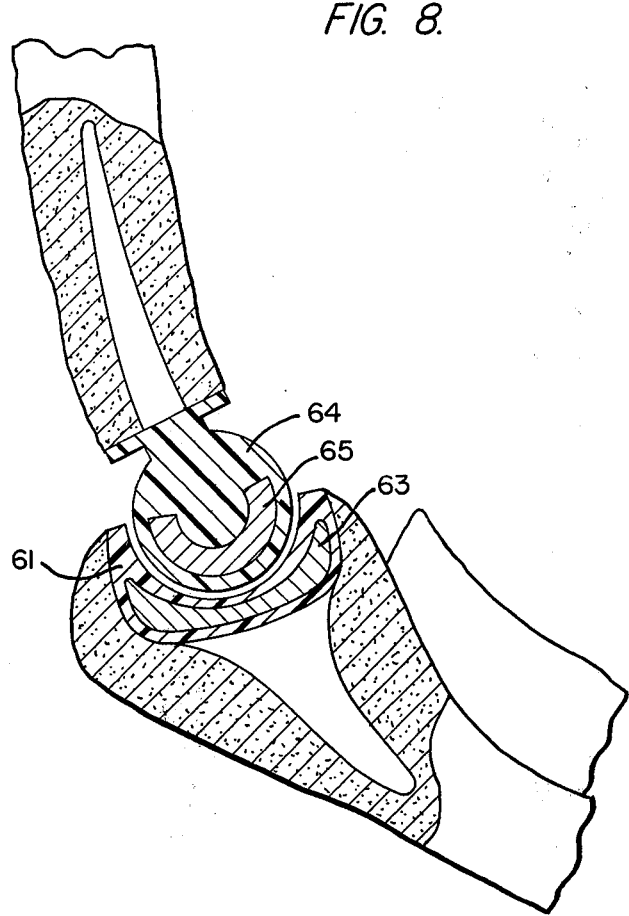
Figure 9:
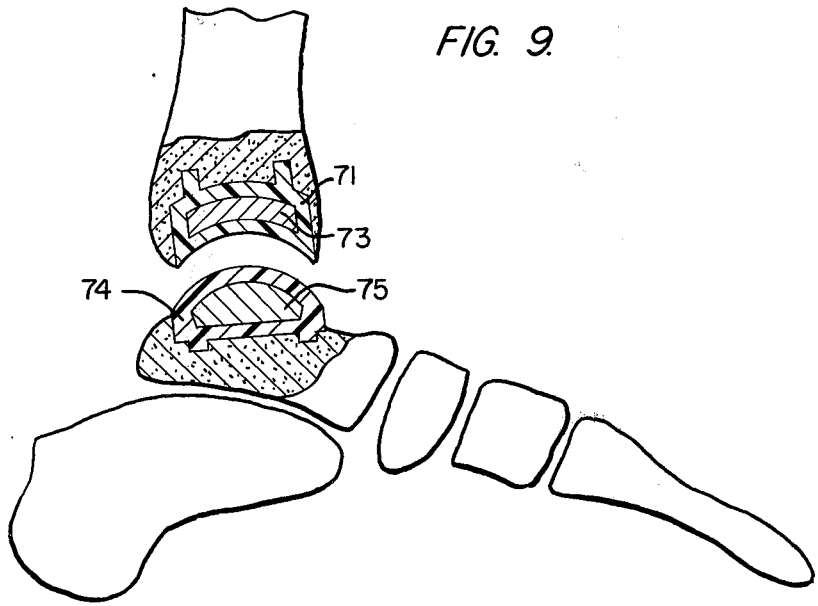

In the interphalangeal joint shown in FIG. 6, the wrist joint shown in FIG. 7 and the elbow joint shown in FIG. 8, the respective magnets 43, 45; 53, 55; and 63, 65 embedded in the respective socket and head portions 41, 44; 51, 54; and 61, 64 are polarized so as to produce attractive forces, while in the ankle joint illustrated in FIG. 9, the permanent magnets 73 and 75 respectively embedded in the socket portion 71 and head portion 74 are polarized for repulsion.

While preferred specific embodiments have been described above and illustrated in the drawings, it is understood, that the shape of the socket and head portions as well as the shape and material of the permanent magnets as well as their disposition in the head and socket portions may be varied in order to simulate the respective joint to be replaced as closely as possible. As particularly shown for the shoulder joint illustrated in FIG. 5, it is possible to use joint portions having considerably different co-operating surfaces. Moreover, as may again be particularly useful in the case of a shoulder joint, the radius of curvature of the concave socket surface may be greater than that of the convex head surface. A considerable freedom of movement similar to that of a natural shoulder joint is thus achieved. Although there is practically only a point contact between the two joint portions, these portions are sufficiently held together by the attraction forces of the permanent magnets.

What is claimed is:

1. An artificial joint for implantation into the living body, comprising a head portion and a socket portion each adapted to be fixedly connected to the respective bone, at least one of said head and socket portions including at least one permanent magnet and the other portion consisting at least partly of a ferromagnetic material, said head and socket portions being shaped so as to permit their mutual rotation about at least one axis as well as a mutual translatory movement along at least one direction transverse to said axis, wherein at least one permanent magnet is included in both said head and socket portions, said permanent magnets being polarized so as to create a repulsion force between said head and socket portions.

2. The artificial joint of claim 1, wherein said at least one permanent magnet is so disposed and shaped that the magnetic force created between itself and said ferromagnetic material tends to counteract the gravitational force exerted on one of head and socket portions.

3. The artificial joint of claim 1, wherein said at least one permanent magnet is made from an alloy comprising cobalt and a rare earth.

4. The artificial joint of claim 1, wherein said at least one permanent magnet and said ferromagnetic material are completely embedded in a material tolerated by the body.

5. The artificial joint of claim 1, wherein said socket portion has a greater radius of curvature about at least one axis than said head portion.

6. The artificial joint of claim 1, wherein said socket portion has a concave surface and said head portion has a convex portion engaging said concave surface, the area of said convex surface being substantially greater than that of said concave surface.

7. An artificial hip joint for implantation into the living body, comprising a substantially hollow-spherical socket portion adapted to be anchored in the pelvis and a substantially spherical head portion adapted to be anchored in the femur, said socket portion and said head portion each including a substantially hollow-spherical permanent magnet, said permanent magnets being polarized so as to repel each other, said head and socket portions being shaped so as to permit a limited movement of said head portion in a direction out of said socket portion.

8. An artificial knee joint for implanation into the living body, comprising a trough-shaped socket portion adapted to be anchored in the tibia and a substantially cylindrical head portion adapted to be anchored in the femur, the trough shape of said socket portion including a first cylindrical portion receiving said head portion in the straight position of said knee joint, a second cylindrical portion receiving said head portion in the rectangularly bent position of said knee joint, and a third portion connecting said first and second cylindrical portions, the radius of curvature of said first and second cylindrical portions being slightly greater than the radius of curvature of said head portion and the radius of curvature of said third portion being essentially greater than said radius of curvature of said first and second cylindrical portions, each of said head and socket portions including a substantially hollow-spherical permanent magnet, said magnets being polarized so as to attract each other.

9. The artificial knee joint of claim 8, wherein said permanent magnets are sized so as to tend to prevent a rotation of said knee joint beyond its completely straight position.

10. An artificial shoulder joint for implantation into the living body, comprising a socket portion adapted to be anchored in the scapula and having a substantially spherical concave surface, and a substantially spherical head portion adapted to be anchored in the humerus, said socket portion including a block-shaped permanent magnet and said head portion including a substantially hollow-spherical permanent magnet, both said permanent magnets being polarized so as to attract each other, the surface of said head portion being substantially greater and having a smaller radius of curvature than said spherical concave surface of said socket portion, wherein the permanent magnet included in said head portion has a thickness increasing towards its upper end.

11. An artificial joint for implantation into the living body, comprising a head portion and a socket portion each adapted to be fixedly connected to a respective bone, each of said head and socket portions including at least one polarized magnet, said head and socket portions being shaped so as to permit their mutual movement with respect to one another, said magnets being polarized so as to create a repulsion force between said head and socket portions.

12. The artificial joint according to claim 11, wherein said polarized magnets include at least one permanent magnet made from an alloy comprising cobalt and a rare earth.

13. The artificial joint according to claim 12, wherein said rare earth is samarium.

14. The artificial joint according to claim 11, wherein at least one of said polarized magnets is completely embedded in a material tolerated by the body.

15. The artificial joint according to claim 12, wherein at least one of said polarized magnets is completely embedded in a material tolerated by the body.

16. The artificial joint according to claim 15, wherein said rare earth is samarium.

17. An artificial joint for implantation into the living body, comprising a head portion and a socket portion each adapted to be fixedly connected to a respective bone, at least one of said head and socket portions including at least one polarized magnet and the other portion consisting at least partly of one of a ferromagnetic material and a polarized magnet, said head and socket portions being shaped so as to permit their mutual movement with respect to one another, at least one of said polarized magnets having an increasing thickness in a direction corresponding to predetermined movement of said head and socket portions with respect to one another, whereby variable magnetic forces are applied to aid said movement.

18. The artificial joint according to claim 17, wherein said polarized magnets include at least one permanent magnet made from an alloy comprising cobalt and a rare earth.

19. The artificial joint according to claim 18, wherein said rare earth is samarium.

20. The artificial joint according to claim 17, wherein at least one of said polarized magnets is completely embedded in a material tolerated by the body.

21. The artificial joint according to claim 18, wherein at least one of said polarized magnets is completely embedded in a material tolerated by the body.

22. The artificial joint of claim 17, wherein said at least one permanent magnet is so disposed and shaped that the magnetic force created between itself and said ferromagnetic material is at a maximum in a position of said joint corresponding to a basic body position.

* * * * *